(12) United States Patent
Chevallier et al.

(10) Patent No.: US 7,963,949 B2
(45) Date of Patent: *Jun. 21, 2011

(54) SAFETY ASSEMBLY FOR A SYRINGE

(75) Inventors: Stéphane Chevallier, Saint-Soupplets (FR); Jean-Michel Chevallier, Enghien-les-Bains (FR)

(73) Assignee: Sanofi-Aventis, Paris (FR)

( * ) Notice: Subject to any disclaimer, the term of this patent is extended or adjusted under 35 U.S.C. 154(b) by 294 days.
This patent is subject to a terminal disclaimer.

(21) Appl. No.: 12/228,781

(22) Filed: Aug. 14, 2008

(65) Prior Publication Data

US 2008/0312603 A1 Dec. 18, 2008

Related U.S. Application Data

(63) Continuation of application No. 10/149,178, filed as application No. PCT/FR00/03397 on Dec. 7, 2000, now Pat. No. 7,429,256.

(30) Foreign Application Priority Data

Dec. 7, 1999 (FR) ..................................... 99 15387

(51) Int. Cl.
*A61M 5/32* (2006.01)
(52) U.S. Cl. ........................................ 604/198; 604/110
(58) Field of Classification Search .................. 604/110, 604/192, 198, 194, 197; 128/919
See application file for complete search history.

(56) References Cited

U.S. PATENT DOCUMENTS

| | | | |
|---|---|---|---|
| 3,306,290 A | 2/1967 | Weltman | 128/218 |
| 4,767,413 A | 8/1988 | Haber et al. | 604/198 |
| 4,820,275 A | 4/1989 | Haber et al. | 604/198 |
| 4,923,447 A | 5/1990 | Morgan | 604/198 |
| 4,927,416 A | 5/1990 | Tomkiel | 604/198 |
| 4,932,947 A | 6/1990 | Cardwell | 604/198 |
| 4,955,868 A | 9/1990 | Klein | 604/198 |
| 5,059,184 A | 10/1991 | Dyke | 604/198 |
| 5,088,986 A | 2/1992 | Nusbaum | 604/195 |
| 5,163,918 A | 11/1992 | Righi et al. | 604/198 |
| 5,176,656 A | 1/1993 | Bayless | 604/198 |
| 5,201,708 A | 4/1993 | Martin | 604/110 |

(Continued)

FOREIGN PATENT DOCUMENTS

EP 0 405 039 A1 1/1991

(Continued)

OTHER PUBLICATIONS

Litigation Information Disclosure Statement filed Feb. 19, 2008, in parent case U.S. Appl. No. 10/149,178, filed Jun. 7, 2002.

*Primary Examiner* — Theodore J Stigell
(74) *Attorney, Agent, or Firm* — McDonnell Boehnen Hulbert & Berghoff LLP

(57) ABSTRACT

A safety support device for a syringe comprises a support sheath (16) for the body (10) of the syringe and an inner sheath (18) suitable for sliding relative to the support sheath between a waiting, retracted position and the extended position for protecting the needle (14) of the syringe. The device has means for holding the syringe body (10) relative to the support sheath (16) and retaining means (30, 32, 22) suitable for being activated to retain g the inner sheath in the waiting, retracted position inside the support sheath and for being deactivated by the piston (12) of the syringe to allow the inner sheath (18) to extend into its protective, extended position.

11 Claims, 5 Drawing Sheets

U.S. PATENT DOCUMENTS

| | | | |
|---|---|---|---|
| 5,201,720 A | 4/1993 | Borgia et al. | 604/198 |
| 5,242,416 A | 9/1993 | Hutson | 604/192 |
| 5,242,420 A | 9/1993 | Martin | 604/198 |
| 5,273,541 A | 12/1993 | Malenchek | 604/110 |
| 5,342,320 A | 8/1994 | Cameron | 604/192 |
| 5,433,712 A | 7/1995 | Stiles et al. | 604/197 |
| 5,492,536 A | 2/1996 | Mascia | 604/197 |
| 5,562,624 A | 10/1996 | Righi et al. | 604/110 |
| 5,562,626 A | 10/1996 | Sanpietro | 604/110 |
| 5,573,513 A | 11/1996 | Wozencroft | 604/198 |
| 5,591,138 A | 1/1997 | Vaillancourt | 604/263 |
| 5,624,400 A | 4/1997 | Firth et al. | 604/110 |
| 5,695,475 A | 12/1997 | Best, Jr. et al. | 604/198 |
| 6,030,366 A | 2/2000 | Mitchell | 604/192 |
| 6,159,184 A | 12/2000 | Perez et al. | 604/192 |
| 6,171,283 B1 | 1/2001 | Perez et al. | 604/192 |
| 6,186,980 B1 | 2/2001 | Brunel | 604/110 |
| RE37,439 E | 11/2001 | Firth et al. | 604/110 |
| 6,319,233 B1 * | 11/2001 | Jansen et al. | 604/192 |
| 6,319,234 B1 * | 11/2001 | Restelli et al. | 604/198 |
| 6,585,702 B1 * | 7/2003 | Brunel | 604/263 |
| 6,613,022 B1 | 9/2003 | Doyle | 604/192 |
| 6,623,459 B1 | 9/2003 | Doyle | 604/197 |
| 7,101,355 B2 | 9/2006 | Doyle | 604/192 |
| 7,429,256 B2 * | 9/2008 | Chevallier et al. | 604/110 |
| 2005/0148943 A1 | 7/2005 | Chevalier | 604/198 |

FOREIGN PATENT DOCUMENTS

| | | |
|---|---|---|
| EP | 0966983 | 12/1999 |
| FR | 2654346 | 5/1991 |
| FR | 2778853 | 11/1999 |
| JP | 11319090 | 11/1999 |
| WO | WO 91/18634 | 12/1991 |
| WO | WO 93/00949 | 1/1993 |
| WO | WO 93/17732 | 9/1993 |
| WO | WO 98/35714 | 8/1998 |
| WO | WO 99/17823 | 4/1999 |
| WO | WO 99/32177 | 7/1999 |
| WO | WO 99/37345 | 7/1999 |
| WO | WO 00/33900 | 6/2000 |
| WO | WO 00/76565 | 12/2000 |
| WO | WO 01/41841 | 6/2001 |

* cited by examiner

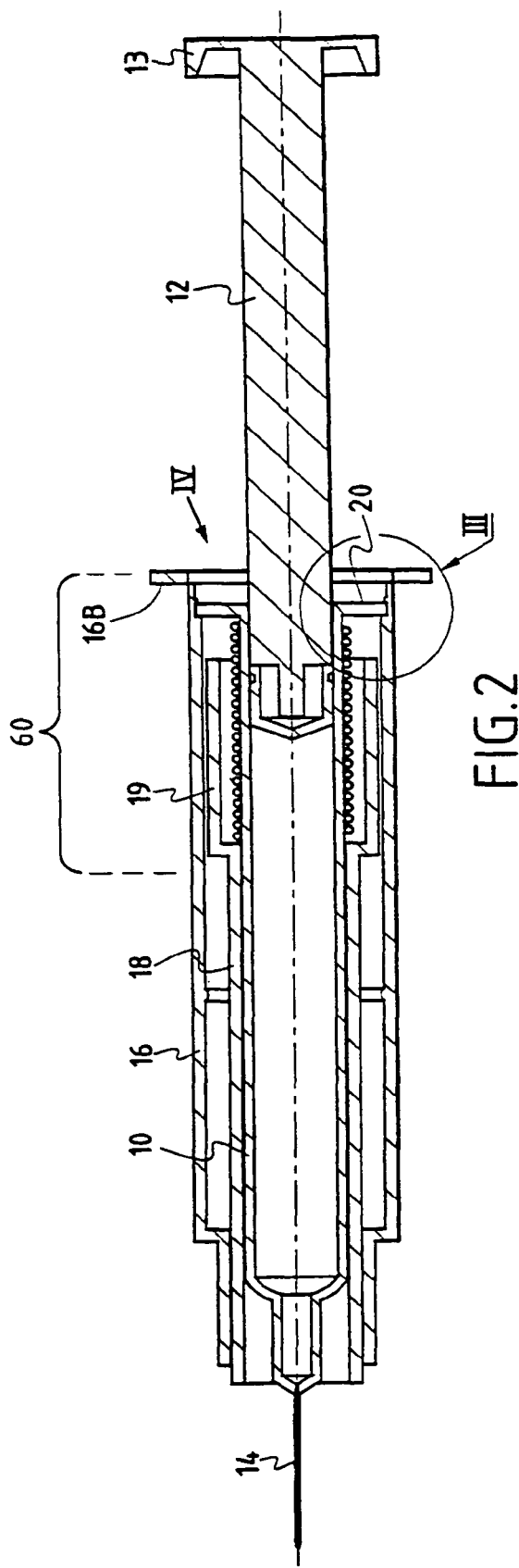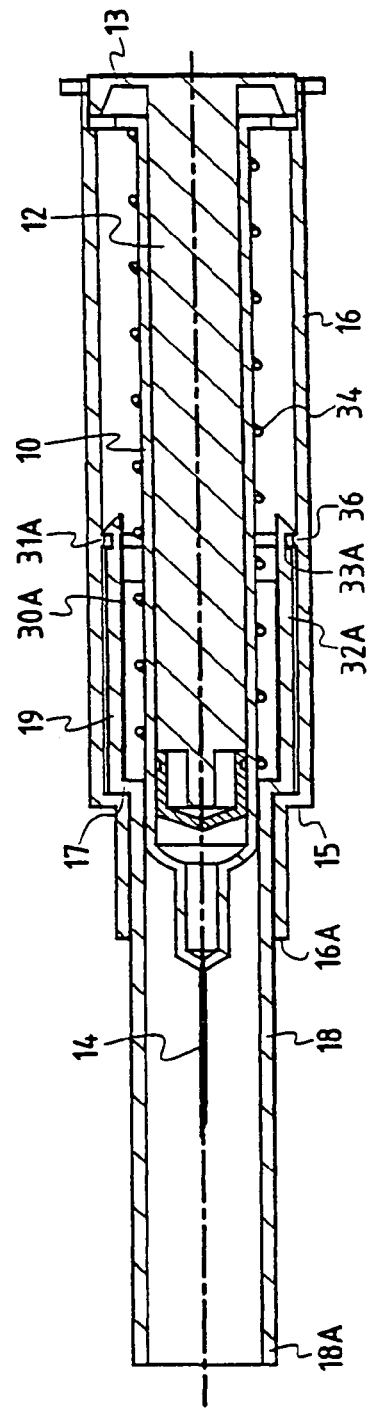

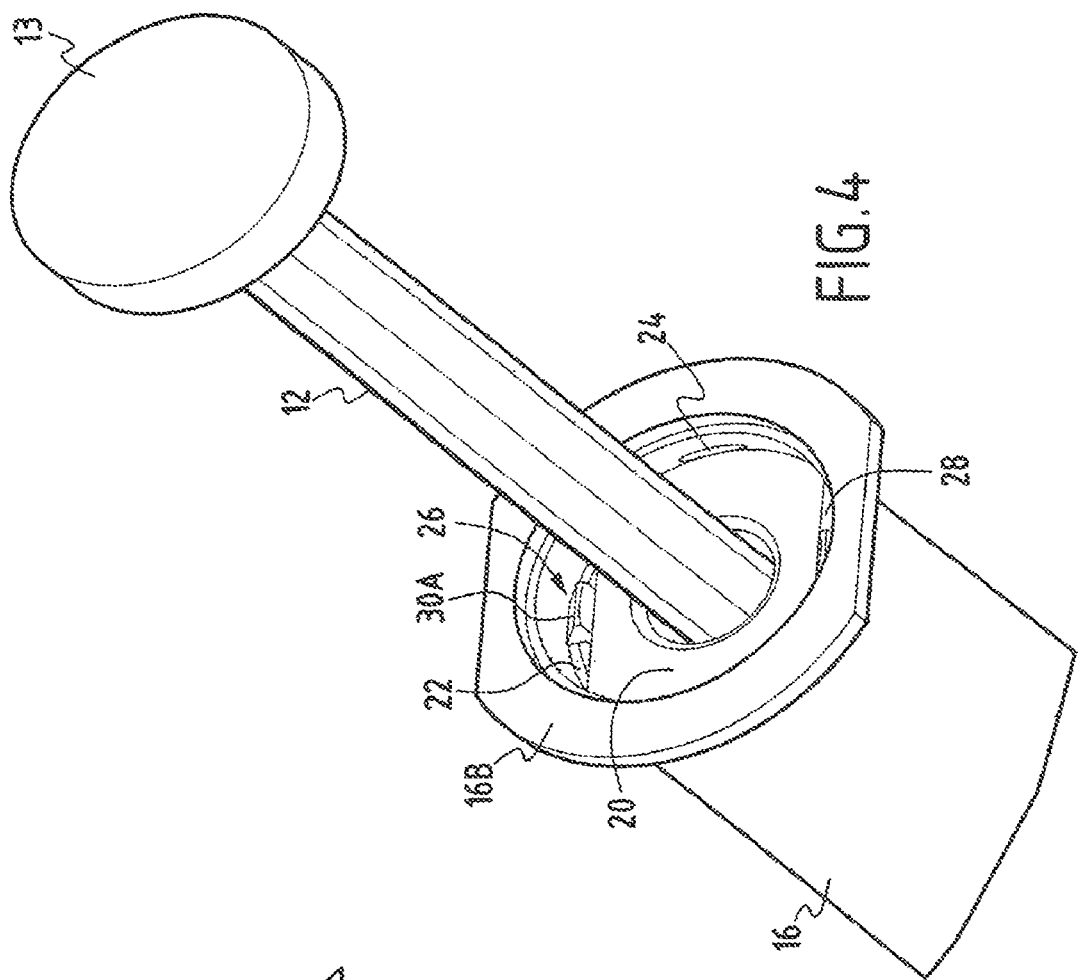
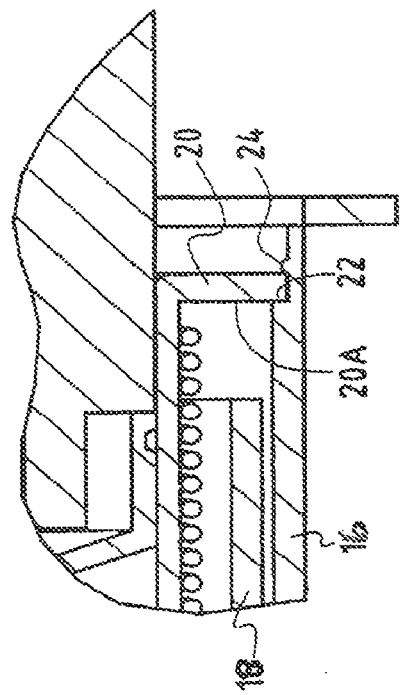
FIG. 3
FIG. 4

SAFETY ASSEMBLY FOR A SYRINGE

The present invention relates to an assembly comprising a safety support device for a syringe and a syringe having a body presenting a collar, a piston, and a needle, the device comprising a support sheath for the syringe body and safety means comprising an inner sheath capable of sliding relative to the support sheath between a waiting, retracted position in which it is substantially retracted inside the support sheath and is suitable for being placed around at least an end portion of the syringe body carrying the needle, and a protective, extended position in which it projects beyond the support sheath to provide protection around the needle, the device further comprising retaining means suitable for being activated to retain the inner sheath in the waiting, retracted position inside the support sheath and for being deactivated to allow the inner sheath to be extended under drive from thrust means.

U.S. Pat. No. 5,492,536 shows an assembly in which a protective shield is formed by resilient strips placed around the syringe body and initially retained in a waiting position by detachable retaining means. At the end of its stroke, the piston detaches these retaining means and under drive from a thrust spring, the shield advances over the syringe body in such a manner that the strips close around the needle.

That system operates only if it is handled properly, it being necessary for the user to take care that the position of the user's fingers on the syringe does not impede movement of the shield. In addition, the strips run the risk of pinching the patient's skin as they close around the needle.

U.S. Pat. No. 5,562,626 shows a system in which the sheath is in the form of a tube retained on a collar of the syringe by resilient tabs. At the end of its stroke, the piston detaches these tabs from the collar, thus enabling the syringe body to be retracted inside the sheath body. In that case also, safety is guaranteed only if the user handles the system with care. The user holds the system via the sheath, generally gripping it, between the index and middle fingers, while pressing in the piston with the thumb. The syringe body can be retracted only if the user moves the thumb away from the sheath far enough to allow the needle to be retracted fully into the sheath.

European patent application No. 0 405 039 presents a system of the same type, presenting substantially the same drawbacks.

Document EP 0 966 983 describes an assembly comprising a safety support device for a syringe and a syringe in which the body is supported in the support sheath in such a manner as to be movable relative thereto. It is this movement which, at the end of injection, serves to trigger extension of the inner sheath. To give rise to this movement, the operator must exert considerable pressure on the syringe after injecting the substance contained therein, thereby causing the needle to penetrate further and running the risk of being painful or even dangerous for the patient.

The invention seeks to propose a safety support device and an assembly constituted by a device of this type and a syringe that enable the above-specified drawbacks to be remedied.

The assembly of the invention achieves this object by the fact that it has holding means suitable for holding the syringe body relative to the support sheath, said holding means comprising an abutment surface and a snap-fastening rib formed on the inside of the support sheath and between which the collar is suitable for being held, and in that the retaining means are suitable for being deactivated as a function of the position of the piston of the syringe.

In the invention, the support sheath and the inner sheath form two concentric tubes, so to speak. The syringe body is engaged inside these tubes, being held relative to the support sheath which constitutes the outer tube, in such a manner that the syringe body remains fixed inside the support sheath. This holding device ensures that the inner sheath is controlled in a manner that is reliable and completely painless for the patient. The user handles the device by taking hold of the support sheath (e.g. gripping it between the index and middle fingers) and by pushing in the syringe piston so as to make the injection, e.g. by means of the thumb. When the syringe piston reaches the desired position (end of stroke), the means for retaining the inner sheath inside the support sheath are deactivated, thus enabling the inner sheath to be extended automatically out from the support sheath. The inner sheath is triggered to cause it to be moved into its protective, extended position directly by the piston when the piston reaches the end of its stroke. At the end of injection, the user does not need to perform any additional movement to enable the inner sheath to be extended, all the user needs to do is continue with the action that was being implemented to make the injection, which action is habitual for the practitioner. Furthermore, no special precautions need to be taken as to how the fingers are positioned on the support sheath and on the piston in order to ensure that the inner sheath is extended.

In a particularly advantageous disposition, the support sheath has a rear end portion and a main portion, said rear portion presenting holding means for the collar of the body of the syringe and a bearing surface for the thrust means.

Advantageously, the support sheath, the inner sheath, and the thrust means form a unit in which the syringe body can be inserted by axial thrust until the collar of said body co-operates with said holding means.

The thrust means advantageously comprise a spring and its stiffness or pre-loading is preferably limited to values that are weak enough to ensure that the inner sheath, on being extended, does not exert disagreeable thrust on the patient's skin.

The device advantageously further comprises locking means suitable for locking the inner sheath in its protective, extended position.

Once extension of the inner sheath has been triggered by deactivating the retaining means, the thrust means have the effect of causing the inner sheath to adopt the position in which it is locked by the locking means. This avoids any risk of untimely retraction of the inner sheath into the support sheath.

The locking means advantageously comprise a locking surface formed on the inner periphery of the support sheath and at least one locking element integral with the inner sheath and suitable for co-operating with said surface when the inner sheath is in the protective, extended position.

This constitutes a simple technique for implementing the above-mentioned locking means.

In an advantageous disposition, the retaining means comprise resilient tongues and retaining surfaces, said tongues or said surfaces being integral with the inner sheath, the tongues being retained on the retaining surfaces in their active, retaining configuration, and being suitable for being moved resiliently towards their inactive configuration in which they escape from said surfaces.

Advantageously, the resilient tongues are oriented substantially axially, are integral with the inner sheath, and co-operate in their active configuration with retaining surfaces formed on the inner periphery of the support sheath.

The axial tongues are preferably disposed in such a manner that a piston actuation portion (e.g. the piston head) comes into contact therewith at the end of the piston stroke, so as to urge them towards their inactive configuration.

The axial tongues are advantageously formed integrally with one or other of the inner and outer sheaths.

In a particularly advantageous embodiment, these resilient tongues are integral with the inner sheath and also constitute locking elements suitable for co-operating with the locking surface when the inner sheath is in the protective, extended position.

The resilient tongues made in this way serve not only for retaining the inner sheath inside the support sheath in the waiting position, but also for locking it in the extended position.

The inner and outer sheaths are advantageously made of plastics material. In an advantageous disposition, at least a portion of the support sheath is made of an opaque material. This precaution serves to mask the internal mechanism of the support device (holding means, spring, . . . ) from the eyes of the patient.

The invention will be well understood and its advantages will appear better on reading the following detailed description of an embodiment given by way of non-limiting example.

The description refers to the accompanying drawings, in which:

FIG. 2 is an axial section on line II-II of FIG. 1;

FIG. 3 is an enlarged view of zone III of FIG. 2;

FIG. 4 is a fragmentary perspective view seen looking along direction IV marked in FIG. 2;

FIG. 5 is an axial section view analogous to that of FIG. 1, but in which the assembly is shown after the syringe has been used, with the needle thereof being in a protected situation;

Figure 1:
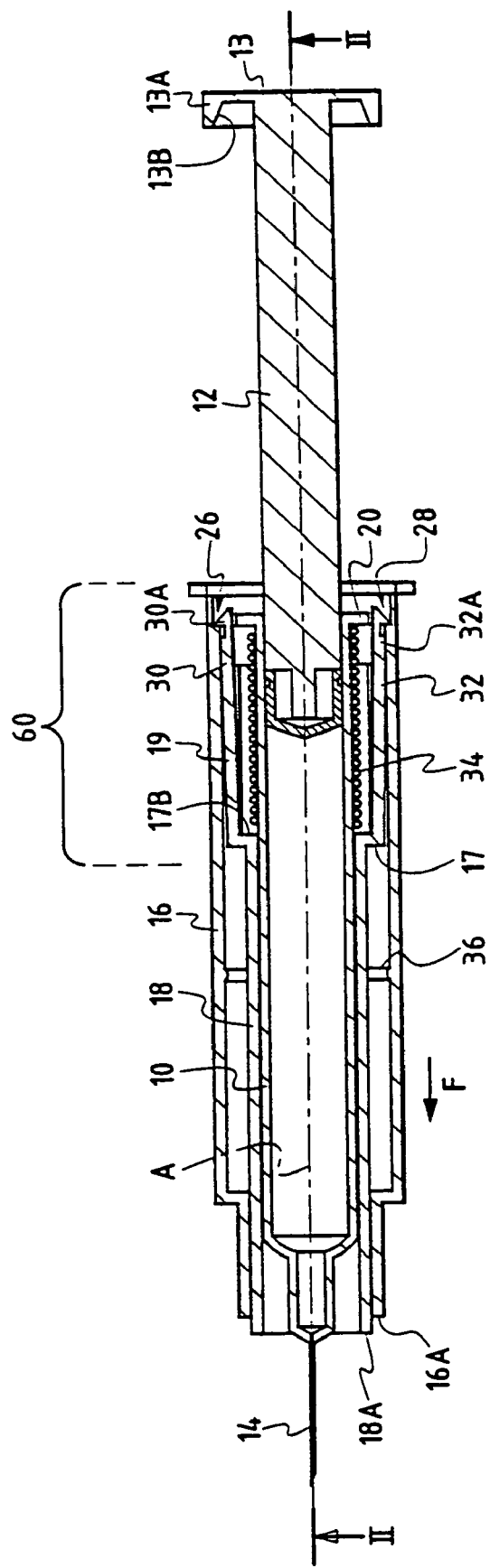
FIG. 1 is an axial section view through a safety support device assembly and a syringe of the invention, in a waiting position before the syringe is used.

The syringe shown in the figures comprises the body 10 in which a piston 12 can slide between an extended position ready for injection as shown in FIG. 1, and a retracted position after injection as shown in FIG. 5. At its end opposite from the piston, an injection needle 14 is connected to the body 10. Conventionally, the syringe body is tubular, being made of glass or of plastics material.

The support device for this syringe comprises an outer support sheath 16 and an inner sheath 18. In the ready position waiting for injection, the inner sheath 18 is generally retracted inside the outer sheath 16, with the syringe body being engaged in said inner sheath 18 and being held relative to the outer sheath 16 in such a manner that the needle 14 projects beyond the front ends 16A and 18A of the sheaths.

Naturally, the front ends are the ends that are for locating close to the injection tip. The forward direction is the direction F along which the piston is thrust.

The syringe body is held relative to the outer sheath 16 by holding means belonging to the sheath, co-operating with a radial collar 20 presented at the rear end (remote from the needle) of the syringe body. As can be seen better in FIGS. 2 and 3, the collar 20 is retained between an abutment surface 22 and a snap-fastening rib 24 provided on the inside of the support sheath 16 (on its inner periphery). The snap-fastening rib 24 is formed behind the abutment surface 22 and while the syringe body is being inserted in the support device, the wall of the sheath 16 deforms elastically to a small extent so as to allow the collar 20 to go past the rib 24. By way of example, the abutment surface 22 is formed on a circular shoulder, while the snap-fastening rib 24 can be formed as a continuous circular bead, or as in the example shown, by two diametrically-opposite rib arcs. To enable it to be held relative to the outer sheath 16, the collar 20 co-operates with the inner periphery of said sheath as described above. Nevertheless, passages are provided between the collar 20 and the inner periphery of the support sheath 16.

These passages 26 and 28 can be seen best in FIGS. 1 and 4. By way of example, the outline of the collar is constituted by a circle of diameter adapted to being held in the sheath 16, which circle is cut along two diametrically opposite chords in order to leave the passages 26 and 28. These passages serve to retain the inner sheath 18 in the ready or waiting position.

As can be seen in FIG. 1, the rear end portion of the sheath 18 carries two axial tongues 30 and 32 whose free ends are hooked onto retention surfaces. Advantageously, as in the example shown, these retention surfaces are formed on the shoulder 22 in zones thereof that are left free by the passages 26 and 28. The snap-fastening ribs 24 are advantageously interrupted in these regions so as to avoid interfering with the free ends of the tongues 30 and 32 hooking onto the shoulder 22.

The tongues 30 and 32 are resilient, and as shown in FIG. 1, they tend naturally to spread apart slightly, going away from the axis A of the device.

The resilient tongues 30 and 32 that are shown are thus integral with the inner sheath 18 and hook onto the outer sheath 16. It would also be possible to arrange for the tongues to be integral with the inner periphery of the outer sheath 16 and for them to hook onto the inner sheath 18, or for the resilient tongues to hook in the opposite direction to that shown in the drawing so as to hook onto the collar 20 of the syringe body. In all of these variants, the tongues must be capable of being released when the piston 12 of the syringe comes to an end-of-stroke position.

The free ends 30A and 32A of the tongues 30 and 32 project a little into the passages 26 and 28. For its part, the piston 12 has an actuation head 13 suitable for co-operating with the free ends 30A and 32A of the tongues so as to urge them into their inactive position.

In the example shown, the tongues 30 and 32 are hooked on the outer sheath 16 and their ends form ramps that face outwards. For its part, the head 13 has a portion in the form of an axial rim 13A extending forwards and having an inner periphery 13B that slopes in such a manner that when the piston reaches the end of its stroke, this inner periphery 13B co-operates with the ramps at the ends of the tongues and urges them towards the axis A. If tongues were used that were formed on the inner periphery of the sheath 16, or if the tongues hook onto the collar 20, then the shape of the actuation head 13 could be modified so that at the end of the stroke of the piston, it would tend to urge the retaining tongues elastically away from the axis A, likewise for the purpose of releasing the inner sheath 18.

Thrust means serve to urge the inner sheath 18 forwards (in the direction F shown in FIG. 1) when the tongues 30 and 32 are released by the piston head. As can be seen in the figures, these thrust means advantageously comprise a spring 34 which, when the syringe is in place in the sheaths, is disposed around the body 10 of the syringe and bears against a first bearing surface belonging to one of the elements constituted by the syringe body and by the support sheath, and on a second bearing surface belonging to the inner sheath.

In the example shown, the bearing surface is formed on the collar 20, with the rear end of the spring 34 resting against the front face 20A of the collar. In its rear portion, the inner sheath 18 has a portion 19 of greater diameter, the portions 18 and 19 being connected together via a shoulder 17. The spring is housed in the annular space that exists inside the portion 19 between the inner sheath 18 and the body 10 of the syringe. The second bearing surface is thus constituted by the rear face 17B of the shoulder 17. The portion 19 is generally tubular in shape and it is split over a fraction of its length so as to constitute the resilient tongues 30 and 32, which tongues also project rearwards relative to the remainder of the rear end of the portion 19.

FIGS. 1 to 4 show the device ready in the waiting, retracted position with the inner sheath 18 inside the sheath 16. In this position, the retaining tongues are hooked and the spring 34 is loaded, while the needle 14 of a syringe placed inside the device projects beyond the front ends of the sheaths.

FIG. 5 shows the device after the syringe has been used. In this position, the piston 12 is at the end of its stroke, its head 13 coming practically into abutment against the collar 20. The head 13 has actuated the tongues 30 and 32 which have released the shoulder 22. The spring 34 has thrust the inner sheath 18 forwards so that it projects well beyond the front end 16A of the support sheath 16, over a length suitable for forming a "protective shield" all around the needle 14 and over a length that is sufficient to prevent any risk of a user coming into contact therewith.

In this situation, the inner sheath 18 is held in its forward position by its shoulder 17 coming into abutment against a shoulder 15 formed in the front region of the outer sheath 16. Behind this shoulder, the inner periphery of the sheath 16 presents a diameter that is suitable for receiving the portion 19 of the sheath 18, while the front end portion 16A of the sheath 16 extending beyond the shoulder 15 presents a diameter that matches the diameter of the portion of the sheath 18 that lies in front of the shoulder 17.

The device of the invention has locking means suitable for locking the inner sheath 18 in this extended position. In other words, these locking means serve to prevent the sheath 18 being retracted into the outer sheath 16 merely by pressing against the free end 18A thereof. These locking means comprise a locking surface formed on the inner periphery of the support sheath 16 and at least one locking element integral with the inner sheath 18 and suitable for co-operating with said locking surface when the inner sheath is in its extended protective position.

In the example shown, the locking surface is constituted merely by an annular bead 36 formed in relief on the inner periphery of the sheath 16. The above-described resilient tongues 30 and 32 also constitute locking elements which co-operate with said locking surface. Beneath the ramps of their free ends, the tongues have outwardly-open setbacks 31A and 33A. The rear faces of these setbacks serve to hook against the shoulder 22, while the front faces thereof serve to lock onto the bead 36.

When a syringe is put into place in the device of the invention, the user handles the assembly constituted by said device and by the syringe by holding the outer sheath 16, e.g. between the index and middle fingers, placing these fingers against a collar 16B formed at the rear end of the sheath and driving the piston by means of the thumb. Once the piston reaches the end of its stroke, it unhooks the tongues 30 and 32 that emerge through the passages 26 and 28, so that the inner sheath is thrust into its extended position in which it is locked by the tongues 30 and 32 co-operating with the bead 36.

The syringe body continues to be held by the above-mentioned holding means. It is also supported against any transverse movement by the contact between its cylindrical outer periphery and the inner periphery of the front portion of the sheath 18.

Figure 6:
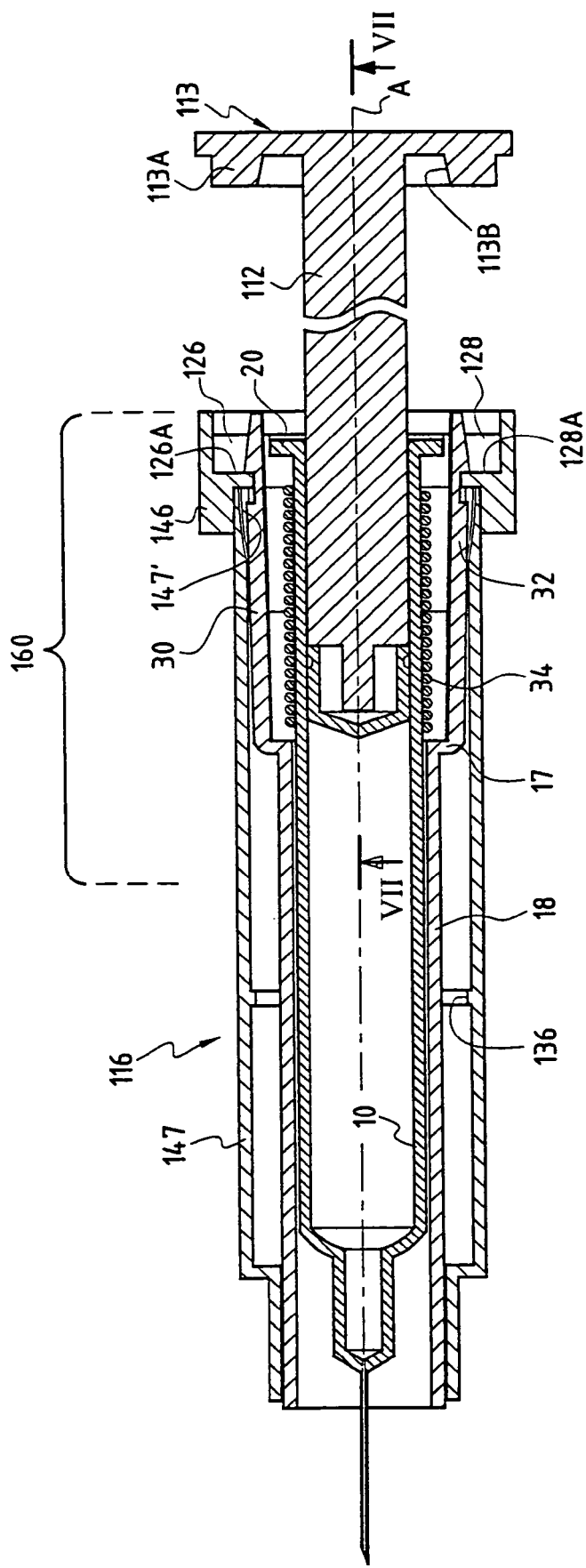
FIG. 6 is a view analogous to FIG. 1 for a variant embodiment.
Figure 7:
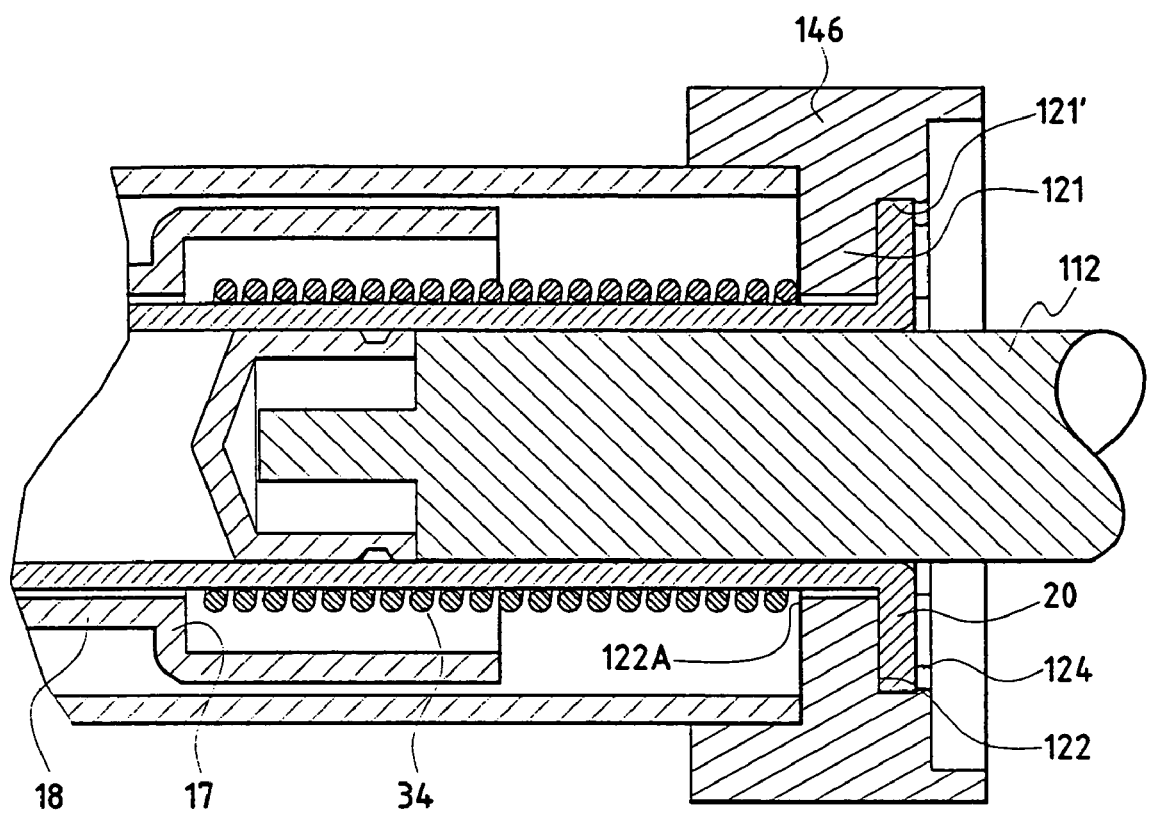
FIG. 7 is a section view on line VII-VII of FIG. 6, on a larger scale.
Figure 8:
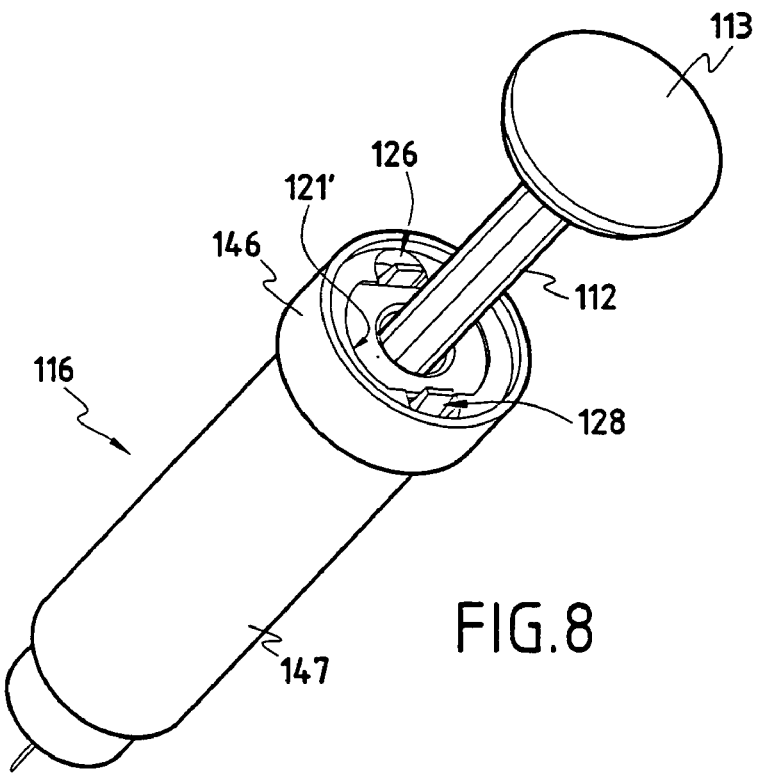
FIG. 8 is a fragmentary perspective view seen looking along arrow VIII of FIG. 6.

In FIGS. 6 to 8, elements that are unchanged compared with those of FIGS. 1 to 5 retain the same references. This variant relates essentially to the way in which the outer sheath is made so as to enable the support device to be delivered in the "loaded" situation, with the user being able to insert the syringe body without needing to take any action on the support itself.

In FIG. 6, the support sheath 116 has an end portion 146 and a main portion 147. The main portion 147 forms a generally cylindrical body which extends over practically the entire length of the support sheath. As for the end portion 146, it is present only towards the rear of the support sheath (its end remote from the needle 14).

Overall, this rear end portion is in the form of a washer which is secured to the free end of the main portion by any appropriate means (heat-sealing, adhesive, . . . ). It presents an inner rib 121 having a rear face that forms an abutment surface 122 against which the collar 20 of the syringe body rests. The washer 146 also presents means forming a snap-fastening rib 124 analogous to the rib 24.

As will be understood on comparing FIGS. 6 and 7, the inner rib 121 presents two arcuate portions defining between them a minimum diametral dimension that is very slightly greater than the outside diameter of the syringe body. The inner rib 121 is thus in the form of a ring having notches 126 and 128 formed therein for allowing the resilient tongues 30 and 32 to pass in order to retain the inner sheath 18. As can be seen more clearly in FIGS. 7 and 8, the rear face of the rib 121 presents a setback zone 121' suitable for receiving the collar 20 which is substantially complementary in shape, thereby holding it angularly.

The tongues 30 and 32 are held relative to the end portion 146. The bottoms of the notches 126 and 128 present respective retaining surfaces 126A and 128A with which the hooking zones of the tongues co-operate.

Thus, in the variant of FIG. 6, the notches 126 and 128 constitute the equivalent of the passages 26 and 28 in the variant of FIGS. 1 to 5. The tongues 30 and 32 project through the notches 126 and 128 and are retained by the retaining surfaces 126A and 128A in such a manner as to be capable of being engaged by the piston head, as described for the variant of FIGS. 1 to 5. The head 113 presents a portion in the form of an axial rim 113A whose inner periphery presents ramps 113B suitable for co-operating with the tongues to move them towards the axis A of the device.

By means of its front face 122A, the inner rib 121 constitutes the first bearing surface for the rear end of the spring.

By means of these dispositions, the support device constituted by the inner and outer sheaths and by the spring can constitute a unit that is sold with its spring loaded, i.e. with the spring pre-stressed between the above-mentioned retaining surface 122A and the shoulder 17 of the inner sheath, which inner sheath is retained by its tongues in the end portion 146 of the support sheath.

The device can be sold in this state to laboratories which then need merely to place a syringe filled with liquid for injection inside the body, the syringe having a conventional piston or optionally a piston whose head has been modified to have the appropriate shape for acting on the tongues 30 and 32 so as to cause the inner sheath to be extended. The bearing surface 122A for the spring extends over a nearly complete circle, with the exception of the notch zones 126 and 128 which are small in size. The spring is thus well supported in its loaded position and its inner periphery defines a channel into which it is easy to insert the syringe body inside the support device. In order to mount the syringe body in its support device, it suffices for the user (the laboratory) to urge the syringe body axially forwards until its collar 20 snap-fastens between the abutment surface 122 and the snap-fastening rib 124.

As can be seen more clearly in FIG. 6, in order to enable the tongues to occupy their splayed-apart position naturally without being impeded by the wall of the main portion 147 of the support sheath, this sheath presents a clear zone 147' in the vicinity of its rear end carrying the end portion 146, with the inside diameter in the clear zone being greater than the remainder of its inside diameter.

The inner periphery of the portion 147 of the sheath 116 presents a rib 136 analogous to the rib 36 in FIGS. 1 to 5, serving to lock the inner sheath 18 in the extended position.

As can also be seen in FIG. 6, the retaining surfaces 126A and 128A for the tongues 30 and 32 are offset forwards a little from the abutment surface 122. This ensures that in order to unlock the inner sheath, it is necessary to insert the head 113 of the piston 112 relatively deeply into the inside of the end portion 146. When the device is sold without a syringe body, and without a piston, this limits any risk of the inner sheath being released in untimely manner since it is difficult to insert a tool accidentally deep enough into the notches 126 and 128 to urge the tongues resiliently inwards.

Advantageously, at least the rear portion 60 or 160 of the support sheath 16 or 116 is made to be opaque so that the mechanism placed inside the sheath is not visible to the patient who is to be injected.

The invention clamied is:

1. A safety syringe support system and syringe combination comprising, in combination,
   a) a syringe comprising a body and a piston having a head portion with an inner periphery and a needle attached at a distal end of the syringe;
   b) a first sheath;
   c) a second sheath, where the first and second sheaths are configured to move relative to each other from a start position to a final position, where one of the sheaths has an inside portion configured to accept and hold the syringe, and where each sheath has a proximal end opposite a distal front end;
   d) at least two resilient tongues extending axially and proximally from the proximal end of one of the sheaths where each tongue terminates in a ramp having a first bearing surface that is configured to engage a second bearing surface on the inner periphery of the head portion of the piston of the syringe at an end of stroke of the piston to cause the tongues to flex radially allowing the sheaths to move relative to each other from the start position to the final position.

2. A safety syringe support system and syringe combination comprising, in combination,
   a) a syringe comprising a body and a piston having a head portion with an inner periphery and a needle attached at a distal end of the syringe;
   b) a first sheath;
   c) a second sheath, where the first and second sheaths are configured to move relative to each other from a start position to a final position, where one of the sheaths has an inside portion configured to accept and hold the syringe, and where each sheath has a proximal end opposite a distal front end;
   d) at least two resilient tongues extending axially and proximally from the proximal end of one of the sheaths to engage the other sheath locking the sheaths in the start position, the tongues being configured to engage the head portion of the piston of the syringe to cause the tongues to flex radially during axial movement of the piston causing the tongues to disengage from the other sheath allowing the sheaths to move relative to each other from the start position to the final position; and
   d) a spring biasing the first and second sheaths and configured to move the sheaths relative to each other from the start position to the final position.

3. The safety syringe support system of claim 2 further comprising a two-part lock having a first part on the first sheath and a second part on the second sheath, where the lock is engaged when sheaths are in the final position preventing the sheaths from moving relative to each other.

4. The safety syringe support system of claim 2 further characterized in that the first sheath completely covers the needle when the sheaths are in the final position.

5. The safety syringe support system of claim 2 further characterized in that the tongues have a hooks that engage the second sheath in the start position.

6. The safety syringe support system of claim 5 further characterized in that the hooks disengage the second sheath when the head engages the tongues.

7. The safety syringe support system of claim 5 further characterized in that the sheaths begin to move relative to each other when the hooks become disengaged from the second sheath.

8. The safety syringe support system of claim 2 further characterized in that one of the sheaths has a finger collar located at the proximal end.

9. The safety syringe support system of claim 2 further comprising two or more two-part locks.

10. A safety syringe support system and syringe combination comprising, in combination,
    a) a syringe comprising a body and a piston having a head portion with an inner periphery and a needle attached at a distal end of the syringe;
    b) a first sheath;
    c) a second sheath, where the first and second sheaths are configured to move relative to each other from a start position to a final position, where one of the sheaths has an inside portion configured to accept and hold the syringe, and where each sheath has a proximal end opposite a distal front end;
    d) a fastener on the second sheath that is configured to engage a collar on the body of the syringe;
    e) at least two resilient tongues extending proximally from a proximal end of one of the sheaths that are configured to cooperate with the head portion of the piston such that when the head engages the tongues the first and second sheaths move relative to each other from the start position to the final position; and
    f) a spring biasing the first and second sheaths and configured to move the sheaths relative to each other from the start position to the final position.

11. A safety syringe support system and syringe combination comprising, in combination,
    a) a syringe comprising a body and a piston having a head portion with an inner periphery;
    b) a first sheath;
    c) a second sheath, where the first and second sheaths are configured to move relative to each other from a start position to a final position, where one of the sheaths has an inside portion configured to accept and hold the syringe, and where each sheath has a proximal end opposite a distal front end;
    d) a two-part lock having a first part on the first sheath and a second part on the second sheath, where the lock is engaged when the sheaths are in the final position preventing the sheaths from moving relative to each other;

e) a fastener on the second sheath that is configured to engage a collar on the body of the syringe;

f) at least two resilient tongues that are configured to cooperate with the head portion of the syringe piston such that when the head engages the tongues the first and second sheaths move relative to each other from the start position to the final position, wherein the tongues have a hooks that engage the second sheath in the start position and where the hooks disengage the second sheath when the head engages the tongues; and g) a spring biasing the first and second sheaths and configured to move the sheaths relative to each other from the start position to the final position.

* * * * *